(12) United States Patent
Ohtsubo et al.

(10) Patent No.: US 6,180,088 B1
(45) Date of Patent: Jan. 30, 2001

(54) FOAMABLE AEROSOL AGRICULTURAL-CHEMICAL COMPOSITION AND METHOD OF CONTROLLING DISEASES AND INSECT PESTS

(75) Inventors: Shigeki Ohtsubo, Konohana-ku; Hiroshi Kodama, Hashimoto; Koji Baba, Kawachinagano; Takehiro Shimada, Nishinomiya; Minoru Fukada, Toyonaka, all of (JP)

(73) Assignee: Nihon Nohyaku Co., Ltd., Tokyo (JP)

( * ) Notice: Under 35 U.S.C. 154(b), the term of this patent shall be extended for 0 days.

(21) Appl. No.: 09/192,594

(22) Filed: Nov. 17, 1998

(51) Int. Cl.[7] .............................. A61L 9/04; A01N 25/34; A01N 25/00
(52) U.S. Cl. .............................. 424/45; 424/405; 424/406
(58) Field of Search .............................. 424/45, 405, 406

(56) References Cited

U.S. PATENT DOCUMENTS 5,055,299 * 10/1991 Dohara et al. ..................... 424/405
5,308,827    5/1994 Sakamoto et al. .

FOREIGN PATENT DOCUMENTS 62-42902    2/1987 (JP) .
7-30117     1/1995 (JP) .
7-119162    5/1995 (JP) .

OTHER PUBLICATIONS

C. Tomlin, Ed., *A World Compendium: The Pesticide Manual; Incorporating the Agrochemicals Handbook*, The Royal Society of Chemistry, Tenth Edition, pp. 9, 591–592, 660–661.

* cited by examiner

*Primary Examiner*—Thurman K. Page
*Assistant Examiner*—Todd D Ware
(74) *Attorney, Agent, or Firm*—Oliff & Berridge, PLC

(57) ABSTRACT

The present invention relates to a foamable aerosol concentrate composition, a foamable aerosol agricultural-chemical composition, and a method of controlling diseases and insect pests; particularly, relates to a foamable aerosol concentrate composition suitable for horticulure as a pastime in which an active ingredient of agricultural-chemicals having insecticidal and/or fungicidal activities and also having systemic action through a plant body and a surfactant are dissolved in glycols that are liquid at normal temperature, a foamable aerosol agricultural-chemical composition including the concentrate composition and a propellant both of which are filled in an aerosol container, a method of controlling diseases and insect pests through spraying application of the foamable aerosol agricultural-chemical composition to stems and/or branches of plants to be treated.

3 Claims, No Drawings

FOAMABLE AEROSOL AGRICULTURAL-CHEMICAL COMPOSITION AND METHOD OF CONTROLLING DISEASES AND INSECT PESTS

BACKGROUND OF THE INVENTION

1. Field of the Invention

The present invention relates to a foamable aerosol concentrate composition, a foamable aerosol agricultural-chemical composition, and a method of controlling diseases and insect pests. More particularly, the present invention relates to a foamable aerosol concenrate composition suitable for horticulure as a pastime in which an active ingredient of agricultural-chemicals having insecticidal and/or fungicidal activities and also having systemic action through a plant body and a surfactant are dissolved in glycols that are liquid at normal temperature; a foamable aerosol agricultural-chemical composition including the concentrate composition and a propellant both of which are filled in an aerosol container; a method of controlling diseases and insect pests through spraying application of the foamable aerosol agricultural-chemical composition to stems and/or branches of plants to be treated.

2. Description of the Related Art

In general, preparations of agricultural chemicals, such as preparations of agricultural chemicals for horticulture as a pastime, are used as formulations of emulsion, wettable powders, granules or aerosol. All these formulations are for sprinkling application agents. They exhibit their effects by being applied either with or without dilution with water on crops or insect pests and weeds to be controlled. However in these applications, large quantity of active ingredients are often wasted as they fail to reach crops or insect pests that are the targets of control. Emulsion, wettable powders and aerosol do not always produce favorable results in view of economic efficiency and environmental sanitation because of their loss at sprinkling or spraying and the adhesion of the agents to men, live stocks and useful things. On the other hand, granules are not scattered in the air, as they are treated on the surface of the soil. However, soil adsorption prevents active ingredients from being absorbed by crops and weeds as the ingredients are adsorbed by the soil. Therefore, large part of applied agents are not used effectively.

In contrast to these preparations of agricultural-chemicals for horticulture as a pastime, agricultural-chemical coatings, in which agents are directly applied to the shaft of plants, are known among general preparations of agricultural chemicals. Quantity of wasted drugs, which cannot reach crops or targets for pest control, is little in agricultural-chemical coatings. Therefore, it is a desirable preparation of agricultural chemicals for economic efficiency and environmental sanitation.

For example, a paste-like agricultural-chemical coating agent described in Japanese Patent Application Laid-open No. Sho 62-42902, in which an agricultural-chemical ingredient is mixed and dispersed in water or an organic solvent together with a film forming agent and a filler, is known as a conventional agricultural-chemical coating agent. However, foamy aerosol spray coating agent has not been known yet.

Recently, agricultural chemicals considering environmental sanitation have been demanded. Especially it has been requested to decrease the application amount of agricultural chemicals as much as possible because of environmental sanitation concern. However, sprinkling and spraying of agricultural chemicals have still been mainly practiced for controlling diseases and insect pests on crops and flowering plants. Agricultural chemical coating agents are desirable in the environmental sanitation aspect as one of solutions of the problem mentioned above. However, currently, it is practiced only for controlling diseases and insect pests of fruit trees. This is because its application needs spreading the paste thinly by the use of a pallet or brush and it is difficult to control the amount of coating. These inconveniences in handling keep agricultural-chemical coatings away from practical use as agricultural chemicals for horticulture as a pastime. Therefore, it is requested to develop preparations of agricultural chemicals which are easier to use while having environmental sanitation benefits mentioned above.

The inventors have invented the present invention by finding out foamable aerosol agricultural-chemical composition and a cocentrate composition for its preparation that have solved the above-mentioned problems. The composition of the present invention is used easily especially in horticulure as a pastime.

BRIEF SUMMARY OF THE INVENTION

An object of the present invention is to provide a foamable aerosol concentrate composition characterized by comprising an active ingredient of agricultural chemicals having a systemic action through a plant body, surfactants and glycols that are liquid at normal temperature, and a foamable aerosol agricultural-chemical composition comprising the foamable aerosol concentrate composition and a propellant.

Another object of the present invention is to provide a novel method of controlling diseases and insect pests by the use of the foamable aerosol agricultural-chemical composition.

The present invention is not limited within horticulure as a pastime that is mainly for home and garden. It includes embodiments used for agricultural and holticultural practice.

DETAILED DESCRIPTION OF THE PREFERRED EMBODIMENTS

A foamable aerosol according to the present invention means one by which an agricultural-chemical composition is jetted from a container together with a propellant so as to be foamingly coated. Foaming mainly takes place at jetting. However, it may take place after jetting. Foaming aerosol is free from scattering and therefore, it can apply larger quantity of drugs to the surface of the target than liquid agricultural chemicals. Furthermore, treated composition has a property of retaining the drugs around the sprayed surface for a long period after treatment.

As usable active ingredients of agricultural chemicals, it can be used any agricultural chemical ingredients which are solid or liquid at normal temperature, have controlling effects on diseases and insect pests of crops and flowering plants, and have a property of exhibiting the effect by a systemic action into a plant body through the treatment on stems and/or branches. Active ingredients of agricultural chemicals will be explained in detailed below. However, the present invention is not limited to them.

Among active ingredients of agricultural chemicals listed in "The Pesticide Manual" (published by British Crop Protection Council, Royal Society of Chemistry), those having systemic action in the section "Mode of action" are given as examples of active ingredients of agricultural chemicals having systemic action through a plant body. Compounds among insecticides having systemic action such as organo-phosphorus insecticides and chloronicotinyl insecticides are the examples of preferable insecticides. Examples of preferable fungicidal agents include compounds having a systemic action among azole antifungal, phenylalanine antifungal and methoxyacrylate antifungal compounds. Following active ingredients of agricultural chemicals can be exemplified as especially preferable compounds. These compounds can be used separately or it is also possible to use two or more compounds at the same time.

(1) (E)-$N^1$-[(6-cholro-3-pyridyl)methyl]-$N^2$-cyano-$N^1$-methylacetamidine (general name: acetamiprid, hereinafter referred to as "compound A")
(2) 1-(6-chloro-3-pyridylmethyl)-N-nitroimidazolidin-2-ylideneamine (general name: imidachloprid, hereinafter referred to as "compound B")
(3) (E)-N-(6-chloro-3-methylpyridylmethyl)-N-ethyl-N'-methyl-2-nitrovinylidenediamine (general name: nitenpyram, hereinafter referred to as "compound C")
(4) O,S-dimethyl acetylphosphoroamidothioate (general name: acephate, hereinafter referred to as "compound D")
(5) Dimethyl (E)-1-methyl-2-(methylcarbamoyl)-vinylphosphate (general name: monocrotophos, hereinafter referred to as "compound E")
(6) Methyl (E)-2-{2-[6-(2-cyanophenoxy)pyridin-4-yloxy]-phenyl}-3-methoxyacrylate (general name: azoxystrobin, hereinafter referred to as "compound F")
(7) (±)-methyl-N-(2-methoxyacetyl)-N-(2,6-xylyl)-DL-alaninate (general name: metalaxyl, hereinafter referred to as "compound G")
(8) Methyl (E)-methoxyimino-[α-(o-tolyloxy)-o-tolyl] acetate (general name: kresoxim-methyl, hereinafter referred to as "compound H")

As surfactants applicable to the present invention, it is exemplified nonionic surfactants such as polyoxyethylene alkylether, polyoxyethylene alkylphenyl ether, polyoxyethylene styrylphenyl ether, sorbitan alkyl ether, polyoxyethylene sorbitan alkyl ether, polyoxyethylene polyoxypropylene blockpolymer and anionic surfactants such as sodium dioctylsulfosuccinate.

Among them, polyoxyethylene alkyl ether and polyoxyethylene polyoxypropylene blockpolymers are preferable.

As glycols which are liquid at normal temperature, ethylene glycol, propylene glycol, hexylene glycol, diethylene glycol, dipropylene glycol, glycerin, polyethylene glycol and polypropylene glycol are given as examples. These glycol compounds can be used separately, or two or more glycols can be used at the same time.

Among them, polyethylene glycol and polypropylene glycol are preferable.

More preferable one is polyethylene glycol 400.

Foamable aerosol concentrate composition of the present invention can be prepared by homogeneously dissolving an active ingredient for agricultural chemical and a surfactant in glycols. The compounding ratio is selected appropriately within the range of 0.1–10 parts by weight of active ingredients of agricultural chemicals, 1–5 parts by weight of surfactant, and 75–98 parts by weight of glycols.

Thickeners, silicones, resins and water repellents can be added to the foamable aerosol stock solution composition according to the necessity.

Then the foamable aerosol agricultural-chemical composition of the present invention comprises 70% or more of foamable aerosol concentrate composition and 30% or less of propellant. It can be prepared by filling the foamable aerosol concentrate composition in an aerosol container. There is no special limitations to propellants, but liquefied gases such as liquefied chlorofluorocarbon gas, propane, butane, liquefied petroleum gas, dimethylether (DME), nitrogen gas and carbonic acid gas are usable.

The foamable aerosol agricultural-chemical composition of the present invention is characterized by jetting the foamable aerosol concentrate composition in the state of foam so as to be coated. Structure of the aerosol container is similar to those for conventional aerosol sprays having a pressure container and a valve. It is preferable to use nozzles the form of which can be selected appropriately according to the purpose; for example, spraying weight can be controlled by spiraling the liquid path in the nozzle; preferably, nozzle can adjust one-time spraying weight to about 0.01–1.0 g; more preferably, the spraying weight can be adjusted to smaller weight, about 0.05–0.5 g.

The foamable aerosol agricultural-chemical composition according to the present invention can control diseases and insect pests through systemic action of the active ingredient of agricultural chemicals into a plant body from the applied foam, which is sprayed to the stems and/or branches of target plants such as cucumbers, eggplants, tomatoes, green pepper, citrus fruits, roses and chrysanthemums.

The following examples illustrate representative examples and test examples. However the present invention is not limited to those examples.

EXAMPLES 1–5

Comparative Examples 1–4, and their Preparation Examples

The unit in Table 1 is part by weight.

TABLE 1

| (Formulation Example) | | | | | |
|---|---|---|---|---|---|
| | Example 1 | Example 2 | Example 3 | Example 4 | Example 5 |
| Compound A | 2 | | | | |
| Compound B | | 2 | | | |
| Compound D | | | 10 | | 5.0 |
| Compound F | | | | 2 | |
| Polyoxyethylene lauryl ether | 4 | 4 | 4 | 4 | |
| Polyoxyethylene polyoxypropylene blockpolymer | | | | | 0.1 |
| Polyvinyl alcohol | | | | | 2.0 |
| Polyethylene glycol 400 | 94 | 94 | 86 | 94 | 92.9 |
| Total | 100 | 100 | 100 | 100 | 100.0 |

| (Comparative Formulation Example) | | | | |
|---|---|---|---|---|
| | Comparative Example 1 | Comparative Example 2 | Comparative Example 3 | Comparative Example 4 |
| Compound D | | | 5.0 | 5.0 |
| Comparative compound a | 5 | | | |
| Comparative compound b | | 2 | | |

TABLE 1-continued

| | | | | |
|---|---|---|---|---|
| Polyoxyethylene lauryl ether | 4 | 4 | | |
| Polyoxyethylene polyoxypropylene block-polymer | | | 0.1 | 0.1 |
| Polyvinyl alcohol | | | 2.0 | 2.0 |
| Polyethylene glycol 400 | 91 | 94 | | |
| Water | | | 92.9 | |
| Diisopropyl-naphthalene | | | | 92.9 |
| Total | 100 | 100 | 100.0 | 100.0 |

Following compounds having no systemic action on a plant body were used as comparative compounds a and b in Table 1.

Comparative compound a: O,O-dimethyl O-4-nitro-m-tolyl phosphorothioate

Comparative compound b: Tetrachloroisophthalonitrile

Preparation Example 1

Preparation Examples of Examples 1–4 and Comparative Examples 1–2

Aerosol concentrate composition was prepared based on the composition described in Table 1. 90 parts by weight of the aerosol concentrate composition and 10 parts by weight of liquefied petroleum gas were filled in an aerosol container to prepare the aerosol agricultural-chemical composition.

Preparation Example 2

Preparation Examples of Example 5 and Comparative Examples 3 and 4

Aerosol concentrate composition was prepared based on the composition described in Table 1. 80 parts by weight of the aerosol concentrate composition and 20 parts by weight of liquefied petroleum gas were mixed and filled in an aerosol container to prepare an aerosol agricultural-chemical composition.

Test Example 1

Test of Controlling Effect on *Macrosiphoniella sanborni* (Gillete)

Foamable aerosol agricultural-chemical compositions prepared according to Preparation Example 1 using the compositions of Examples 1–3 and Comparative Example 1 of the present invention are applied by spraying on the branches (4 mm in diameter) of small chrysanthemum, on which *Macrosiphoniella sanborni* (Gillete) were parasite, at prescribed dosage. Number of parasites on the two branches were investigated before the treatment and 4 days after the treatment and 6 days after the treatment. Table 2 shows the result.

TABLE 2

(Controlling effect on *Macrosiphoniella sanborni* (Gillete))

| Agents provided for test | Dose (g/branch) | Before treatment | | 4 days after treatment | | 6 days after treatment | |
|---|---|---|---|---|---|---|---|
| | | adults | larvae | adults | larvae | adults | larvae |
| Example 1 | 0.2 | 5 | 28 | 0 | 0 | 0 | 0 |
| | 0.1 | 6 | 24 | 0 | 0 | 0 | 0 |
| Example 2 | 0.2 | 8 | 20 | 0 | 0 | 0 | 0 |
| | 0.1 | 6 | 28 | 0 | 0 | 0 | 0 |
| Example 3 | 0.2 | 7 | 18 | 0 | 0 | 0 | 0 |
| | 0.1 | 7 | 22 | 0 | 0 | 0 | 0 |
| Comparative Example 1 | 0.2 | 6 | 19 | 4 | 12 | 3 | 10 |
| | 0.1 | 5 | 25 | 3 | 20 | 4 | 19 |
| Untreatment | — | 6 | 14 | 3 | 22 | 8 | 29 |

Test Example 2

Test for Insecticidal Effect

Effect manifesting rate of the aerosol agricultural-chemical composition of Example 5 was tested in comparison with that of insecticide granules on the market. Small chrysanthemum, on which *Macrosiphoniella sanborni* (Gillete) was parasite, was treated with the prescribed dose of agent. Effect of the treatment was investigated by counting the number of *Macrosiphoniella sanborni* (Gillete) before and after the treatment.

The aerosol agricultural chemicals are prepared according to Preparation Example 2 using a concentrate containing 5% of an active ingredient based on the composition described in Table 1. Weight of single spraying was adjusted to be about 80 mg (weight of the spray container was measured before spraying and after 100-times spraying and amount of single spraying is calculated from the difference; and since this agricultural chemicals are prepared based on Preparation Example 2, content of active ingredient in the aerosol agricultural chemicals is 4%, and therefore, single spray corresponds to the application of 3.2 mg of compound D.). The aerosol agricultural chemicals foam with the adjusted weight was applied to the stem 5–10 cm under where parasites were placed. 5% Acephate granules (on the market) were used for comparison. They were applied near the root so that the quantity of active ingredient of the granules becomes the prescribed dose. Table 3 shows the result.

TABLE 3

(Controlling effect on *Macrosiphoniella sanborni* Gillete)

| Treatment | Number of survived larva | | | | | |
|---|---|---|---|---|---|---|
| | Dosage (AI conversion/plant) | Before treatment | 1 day after treatment | 3 days after treatment | 7 days after treatment | 14 days after treatment |
| Tested region Example 5 | 3.2 mg | 45 | 5 | 1 | 0 | 0 |
| Comparative region Acephate granule | 50 mg | 50 | 72 | 48 | 5 | 0 |
| Untreatment | — | 19 | 36 | 63 | 158 | 1153 |

Test Example 3

Controlling Effect Test Against Powdery Mildew (*Spherotheca fuliginea*)

The foamable aerosol agricultural-chemical compositions of Example 4 and Comparative Example 2 of the present invention were sprayed to the stems of cucumbers (Yotsuba, 2.5 leaf stage) at prescribed dose. Then the plants were stood still in a green house for a week. Six days after the treatment of the agent, the plants were infected with powdery mildew (*Spherotheca fuliginea*). Rate of their outbreak was investigated 10 days after the infection. Preventive value was calculated through the comparison with the untreated group.

At the same time, degree of phytotoxicity was investigated and determined with following standard.

Criteria for determining drug-induced suffering:
−: no phytotoxicity
±: slight browning of leaf edges
+: browning at a part of leaf edges
++: shrinkage and shortening of nodes observed on a whole leaf
+++: cup shaped leaf, withering of cotyledon
++++: withering
Table 4 shows the result.

TABLE 4

(Controlling effect on powdery mildew (*Spherotheca fuliginea*))

| Drugs provided for test | Dosage (g/plant) | Preventive value (%) | Phytotoxicity |
|---|---|---|---|
| Example 4 | 0.1 | 95 | — |
|  | 0.02 | 69 | — |
| Comparative Example 2 | 0.1 | 0 | — |
|  | 0.02 | 0 | — |
| Untreatment | — | 10 | — |

Test Example 4

Stability Test for Ingredients

The aerosol agricultural-chemical composition prepared through Preparation Example 2 using each formulation described in Table 1 was charged in an aerosol container and stored in a constant temperature bath at 50° C. Then content of active ingredient (compound D) was analyzed with a gas chromatography (Anal. Methods Pestic. Plant Grouth Regul., 1973, 7, 363). Residual percentage of active ingredient was obtained using an equation described below.

$$\text{Residual percentage} = \frac{\text{Content after storage}}{\text{Content at preparation}} \times 100$$

Left column of Table 5 shows the result.

Test Example 5

Phytotoxicity Test

The aerosol agricultural-chemical composition prepared through Preparation Example 2 using each formulation described in Table 1 was sprayed to plant bodies (small chrysanthemum) directly. The influence was investigated through visual inspection three days after the spraying. Existence of phytotoxicity was determined by the existence of discoloring. Right column in Table 5 shows the result.

−: Without discoloring and Without phytotoxicity
+: With discoloring and With phytotoxicity

TABLE 5

| Test suffering formulation number | 50° C. - 2 weeks Residual percentage of Compound D (%) | Phytotoxicity of chrysanthemum | | |
|---|---|---|---|---|
| | | stem | leaf | flower |
| Example 5 | 99.5 | − | − | − |
| Comparative Example 3 | 60.2 | − | − | − |
| Comparative Example 4 | 99.0 | − | + | + |

As the aerosol agricultural-chemical composition prepared by using the aerosol concentrate composition of the present invention can be applied in state of foam, it is free from scattering by sprinkling and can be applied to the required part accurately. In the result, it is highly safe for sprinklers. Furthermore, as it shows immediate effect only with a tenth or less weight of granules, it can save amount to be used of agricultural chemicals. Therefore the aerosol agricultural-chemical composition is preferable in environmental sanitation aspect because it is free from scattering and the total application amount of the agricultural chemicals is little. Furthermore, it is excellent as it is free from the problem about the stability of active ingredients and phytotoxicity.

What is claimed is:

1. A foamable aerosol agricultural-chemical composition comprising:

(a) 70 parts by weight or more of a foamable aerosol concentrate composition containing:
      0.1 to 10 parts by weight of an agricultural-chemical active ingredient having insecticidal and/or fungicidal activities and having a systemic action through a plant body in 100 parts by weight of the foamable aerosol concentrate composition,
      1 to 5 parts by weight of a surfactant in 100 parts by weight of the foamable aerosol concentrate composition, and
      75 to 98 parts by weight of polyethylene glycol 400 that is liquid at normal temperature in 100 parts by weight of the foamable aerosol concentrate composition, and (b) 30 parts by weight or less of a liquefied gas.

2. A method of controlling diseases and insect pests, comprising spraying 0.01–1.0 g of the foamable aerosol agricultural-chemical composition as claimed in claim 1 to stems and/or branches of crops or ornamental plants in order to protect the crops or ornamental plants from diseases and insect pests.

3. A method of controlling diseases and insect pests as claimed in claim 2, wherein the crop or the ornamental plant is selected from the group consisting of cucumbers, eggplants, tomatoes, green peppers, citrus fruits, roses and chrysanthemums.

* * * * *